United States Patent [19]

Steer et al.

[11] Patent Number: 5,041,102
[45] Date of Patent: Aug. 20, 1991

[54] OSTOMY COUPLING

[75] Inventors: Peter L. Steer, Sussex; David J. Auld, Surrey, both of England

[73] Assignee: E. R. Squibb & Sons, Inc., Princeton, N.J.

[21] Appl. No.: 465,853

[22] Filed: Jan. 18, 1990

[30] Foreign Application Priority Data

Feb. 3, 1989 [GB] United Kingdom ............... 8902376

[51] Int. Cl.⁵ .............................................. A61F 5/44
[52] U.S. Cl. ..................................... 604/338; 604/342
[58] Field of Search ........................ 604/332, 337–339, 604/342

[56] References Cited

U.S. PATENT DOCUMENTS

| 4,460,363 | 7/1984 | Steer et al. | 604/336 |
| 4,834,732 | 5/1989 | Steer et al. | 604/338 |
| 4,883,477 | 11/1989 | Steer | 604/339 |
| 4,892,530 | 1/1990 | Steer | 604/338 |
| 4,929,245 | 5/1990 | Holtermann et al. | 604/338 |
| 4,950,261 | 8/1990 | Steer | 604/339 |

FOREIGN PATENT DOCUMENTS

| 163979 | 11/1985 | European Pat. Off. | |
| 286501 | 12/1988 | European Pat. Off. | |
| 0313175 | 4/1989 | European Pat. Off. | 604/337 |
| 1568860 | 6/1980 | United Kingdom . | |
| 1571657 | 7/1980 | United Kingdom . | |
| 1586823 | 3/1981 | United Kingdom . | |
| 1586824 | 3/1981 | United Kingdom . | |
| 2183481 | 6/1987 | United Kingdom | 604/342 |
| 2193098 | 2/1988 | United Kingdom . | |
| 2201345 | 9/1988 | United Kingdom . | |
| 2201346 | 9/1988 | United Kingdom . | |
| 2219507 | 12/1989 | United Kingdom . | |

Primary Examiner—Randall L. Green
Assistant Examiner—R. Clarke
Attorney, Agent, or Firm—Robert E. Lee; Gene Warzecha

[57] ABSTRACT

A coupling element system for an ostomy bag including a bag-side coupling element having a stomal orifice surrounded by a channel shaped member, a body-side coupling element having a stomal orifice surrounded by a rib-like member which can make snap-fit engagement with the channel shaped member, and a locking member. The latter member has radially inwardly deformable arms and is rotatable relative to the body-side coupling. The deformable arms are shaped and positioned so that upon rotation of the locking member in one rotary direction relative to the body-side coupling element they are deformed radially inwardly and over-lie a portion of the bag-side coupling element.

The locking member may be generally annular with the arms arcuate in shape each with a blade portion and a leg portion which connects the blade portion to the remainder of the locking member.

12 Claims, 4 Drawing Sheets

OSTOMY COUPLING

BACKGROUND OF THE INVENTION

This invention relates to an ostomy coupling. Ostomy couplings are known. One well-tried and successful coupling system is described and claimed in British Patents Nos. 1,571,657; 1,568,860; 1,586,823 and 1,586,824. More recently, there have been proposals for three-part systems which involve a third part whose main function is to positively lock the other two parts together. Examples of three-part systems are shown in U.K. Published Patent Application Nos. 2,193,098; 2,201,345 and 2,201,346 and European patent Application No. 286501. A further system is suggested in U.K. Application No. 8817995. One disadvantage of all these three-part systems is that their bag-side coupling parts are not compatible with the bag side coupling of the well-tried system referred to above. Consequently, a user who sometimes requires the extra security of a locking system (i.e. when playing games or indulging in other energetic activity) but sometimes merely requires a normal press-together system has to purchase and carry two entirely different systems. Clearly this is an additional and unacceptable burden on ostomates.

It is an aim of this invention to overcome or at least greatly mitigate this problem.

SUMMARY OF THE INVENTION

According to the invention there is provided a coupling system for an ostomy bag including a bag-side coupling element having a stomal orifice surrounded by a channel shaped member, a body-side coupling element having a stomal orifice surrounded by a rib-like member which can make snap-fit engagement with the channel shaped member, and a locking member having radially inwardly deformable arms and which is rotatable relative to the body-side coupling, the deformable arms being shaped and positioned so that upon rotation of the locking member in one rotary-direction relative to the body-side coupling element they are deformed radially inwardly and over-lie a portion of the bag-side coupling element.

In a preferred embodiment of the invention, the locking member is generally annular and the arms are arcuate in shape each with a blade portion and a leg portion which connects the blade portion to the remainder of the locking member. A plurality of arms are spaced around and form the major part of the boundary of a central stomal aperture in the locking member. The body-side coupling preferably has upstanding lugs positioned to engage a part of the radially outer surface of each blade portion, and these lugs may be elongated in a circumferential direction and located so that they are at a small angle to the tangential direction. They may have an inturned roof portion. In use, relative rotation between the locking member and the body-side coupling element causes the flexible arms to be urged radially inwardly as their respective blades slide past the angled lugs. The blade portions of the arms have their radially inner surfaces shaped so that in the locked position these inner surfaces together define a cylindrical surface of diameter substantially equal to the outer diameter of the outer channel wall of the bag-side coupling element.

BRIEF DESCRIPTION OF THE DRAWINGS

The invention will be better understood from the following non-limiting description of an example thereof given with reference to the accompanying drawings in which.

DETAILED DESCRIPTION OF THE DRAWINGS

Figure 1:
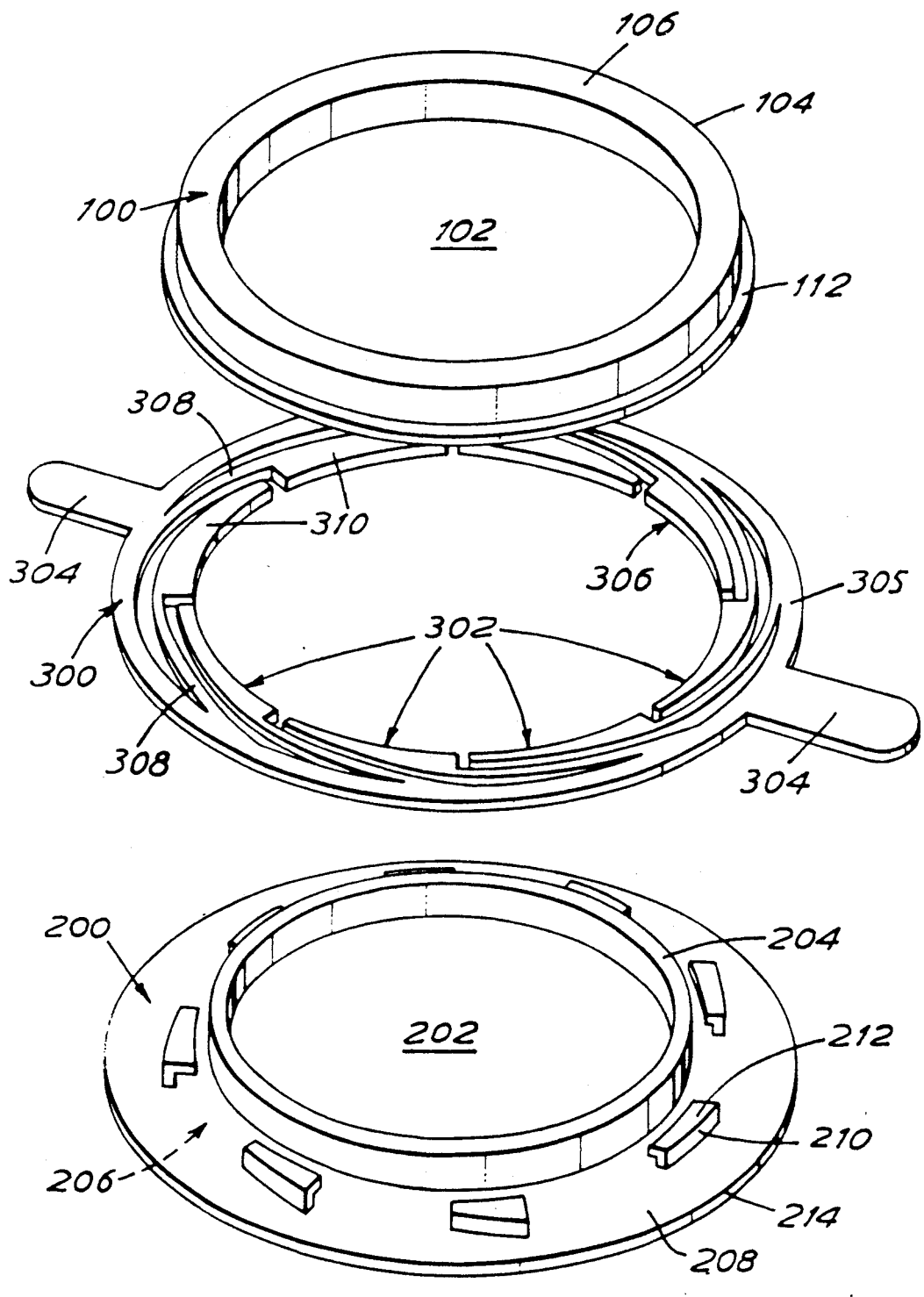
FIG. 1 is an exploded view of one example of an ostomy coupling according to the invention.

In the drawings, like parts are denoted by like reference numerals.

The illustrated coupling system for an ostomy bag includes a bag-side coupling element 100, a body-side coupling element 200 and a locking member 300. The bag-side coupling element 100 has a stomal orifice 102 surrounded by a channel-shaped member 104. The body-side coupling element 200 has a stomal orifice 202 surrounded by a rib-like member 204 which can make a snap-fit engagement with the channel-shaped member 104. The element 200 has a radially outwardly extending flange 208. Lugs 210 extend upwardly from the flange 208 and are located at uniformly arcuately spaced positions around the stomal orifice 202. Each lug is angled and has a roof portion 212. Each lug makes a small angle, e.g. 5 to 15, preferably about 10 degrees, with a tangent to the circular outer periphery 214 of the flange 208. In normal use, as is conventional, the bag-side coupling element 100 is attached via its surface 106 to an ostomy pouch or bag, and the body-side coupling element 200 is attached via its annular surface 206 to a pad of medical grade adhesive material. A suitable medical grade adhesive is that known as "STOMAHESIVE" (Registered Trade Mark). The attachment may be by adhesives or by a plastic welding procedure. For a fuller description of one type of conventional ostomy pouch and coupling is referred to U.S. Pat. No. 4,460,363 which is hereby incorporated by reference as if specifically set forth herein.

The locking member 300 is generally annular in form and has a stomal orifice 302. It also has two readily extending tabs or levers 304, which can be gripped or held by a user when she or he wishes to rotate the locking member 300 relative to the body-side ring 200. The locking member 300 is a simple substantially planar ring 305 having arcuate flexible arms 306 which surround the stomal orifice 302 and which separate from the radially outer portion of the ring 305. It may be made of an acetal resin. Each of these arms comprises a leg portion 308 and a blade portion 310. Each leg portion connects the blade portion to the remainder of the ring 305. The leg portions 308 are relatively thin compared to the remainder of the ring or the blade portions and hence, bearing in mind the inherent resilience of the plastics material from which the locking member is made, the arms can be flexed relative to the locking member ring 300 by applied forces, but tend to return to their rest positions illustrated in FIG. 5 due to the resilience of the material.

The bag-side coupling element 100 is of substantially rectangular U-shaped channel form and has a radially outwardly extending rim or flange 112. This flange in the locked condition of the coupling system is trapped between respective parts of the blade portions 310 which over-lie it and the flange 208 of the body-side coupling element 200. The portion of the blade portion 310 which over-lies flange 112 is found by the difference in thickness of the radially inward portion of the blade portion 310 which is thinner than the radially outer portion which is connected to and extends from the leg portion 308. This is best seen from FIG. 6 which illustrates the plan view of the body side coupling element 200 and locking member 300 and from FIG. 7 where the roof portion 212 of the lug 210 is seen overlying the blade portion 310 of the locking member 300 and the over-lying portion of blade portions 310 is seen over-lying flange 112.

The inner surfaces 314 of the blade portion 310 are arcuate and are shaped so that in the closed condition they define a cylindrical surface which has substantially the same internal diameter as the outer channel wall of the bag-side coupling element 100. That is, viewing FIG. 7, the inner surface 314 of the blade portion is substantially in contact with and substantially follows the shape of the radially outer surface 114 of the outer wall 115 of the channel of the bag-side coupling element 100.

Figure 5:
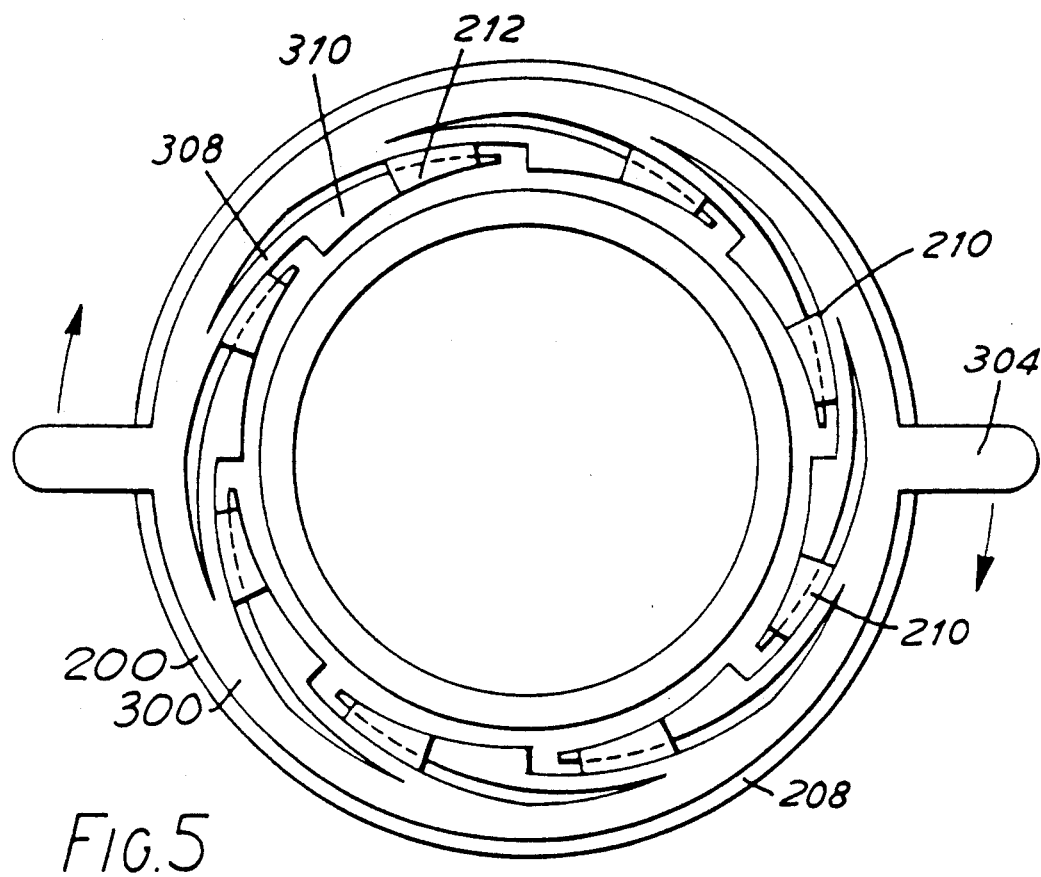
FIGS. 5 and 6 are top plan views corresponding to FIG. 4 respectively showing the locked and unlocked positions.

To assemble the locking member 300 to the body side coupling element 200, the rib-like member 204 is inserted through the stomal orifice 302 formed by the inner surface 314 of the blade portions 310. The roof 212 of the lugs 210 will engage the underside of the blade portions 310, deflecting then upward. Each blade must be deflected radially inwardly by hand toward member 204 so it can clear the roof 212 and snap back into position under the roof 212 with the lug 210 positioned between the corresponding blade portion of one arm and the leg portion of an angularly adjacent arm. With the relative angular positioning of the part 200 and 300 as shown in FIG. 5 there is enough room to deflect the blades inwardly toward rib-like member 204 to allow the blades to clear roof 212. Preferably, the locking member 300 is supplied from the manufacturer already fitted to the body side coupling 200. Since lug 210 has the roof 212, once the parts are fitted they should never become detached in use.

With the locking member 300 and bag-side coupling element assembled as shown in FIG. 5, the body side coupling element 100 is snapped into place such that rib-like member 204 fits into the channel shaped member 104. The flange 112 passes through the enlarged stomal opening 302 without much interference from the blades because with the locking member 300 rotated counter clockwise to the unlock position, the blade portions 310 are not being forced radially inwardly by the lugs 210.

Figure 2:
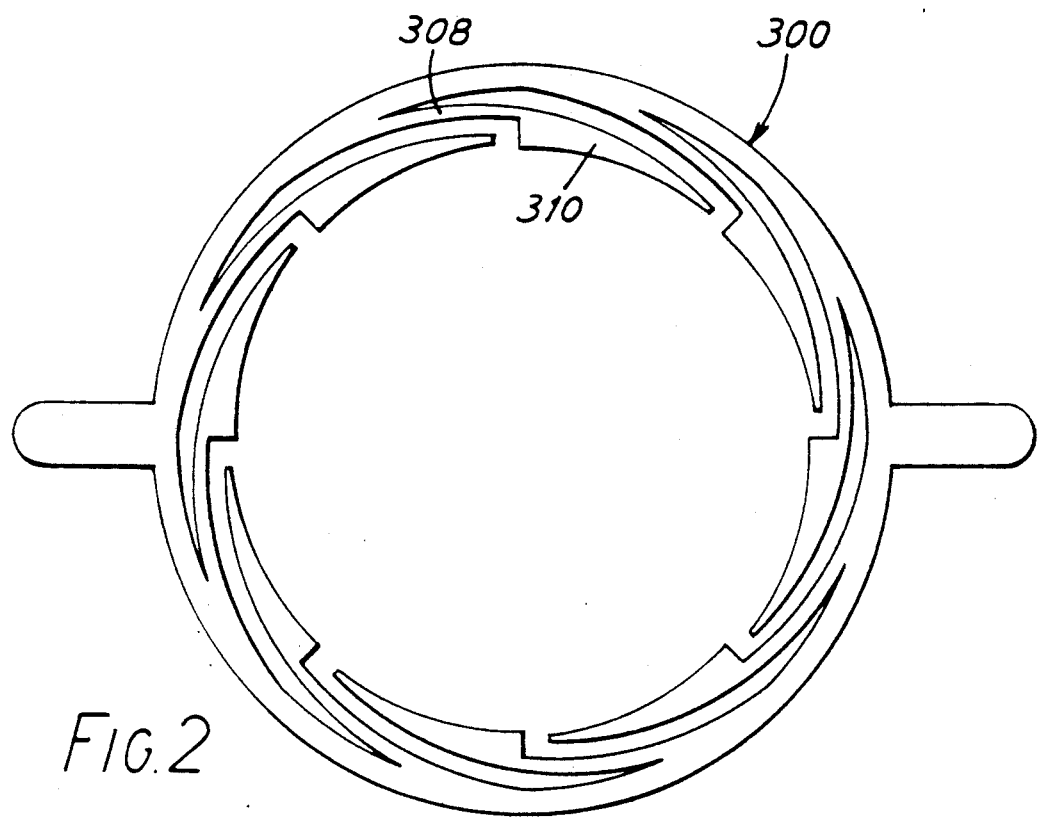
FIG. 2 is a plan view of the locking member shown in FIG. 1.
Figure 3:
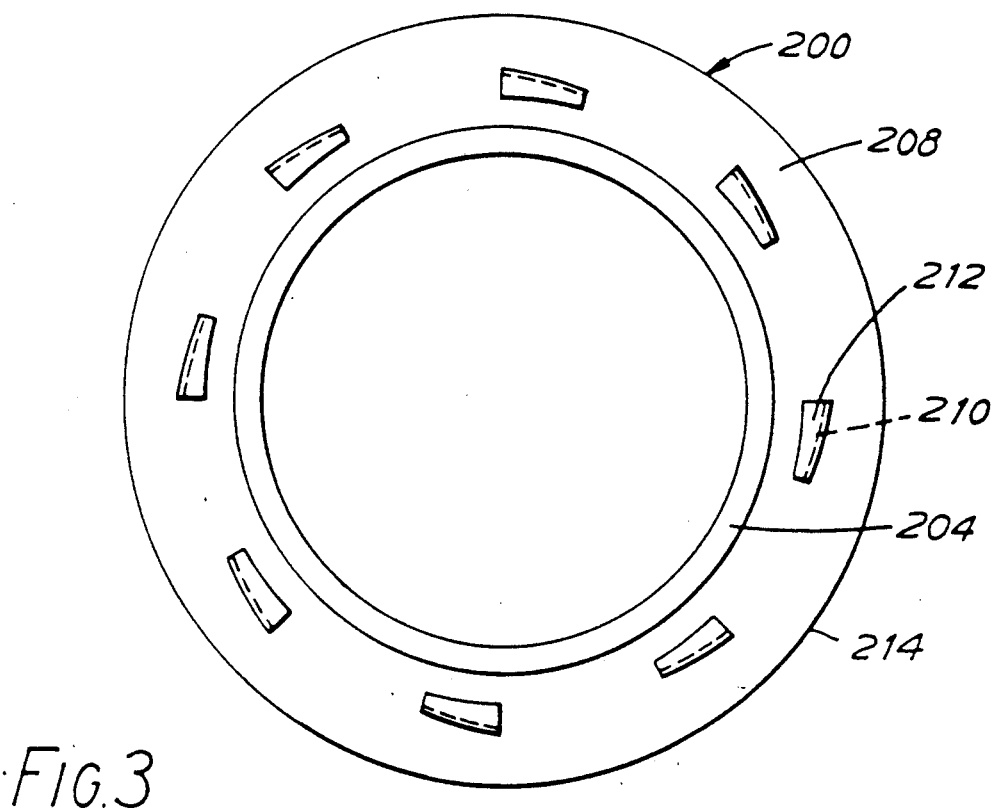
FIG. 3 is a plan view of the body side coupling element showing in FIG. 1.
Figure 6:
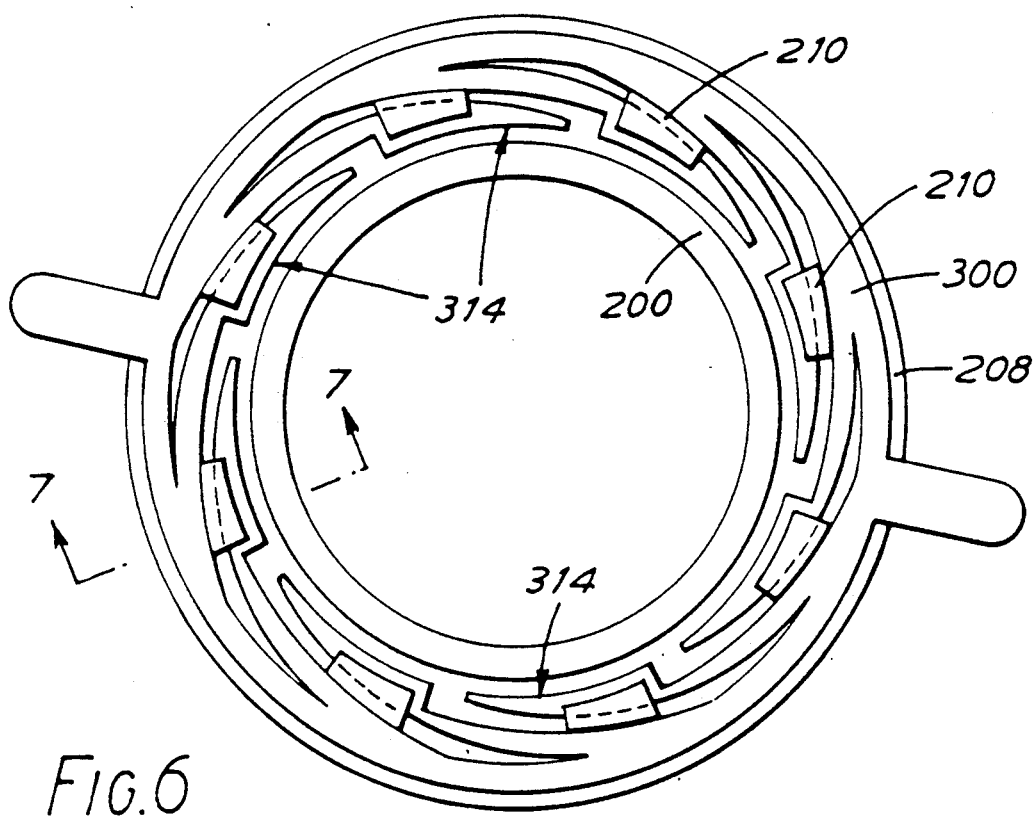
Figure 4:
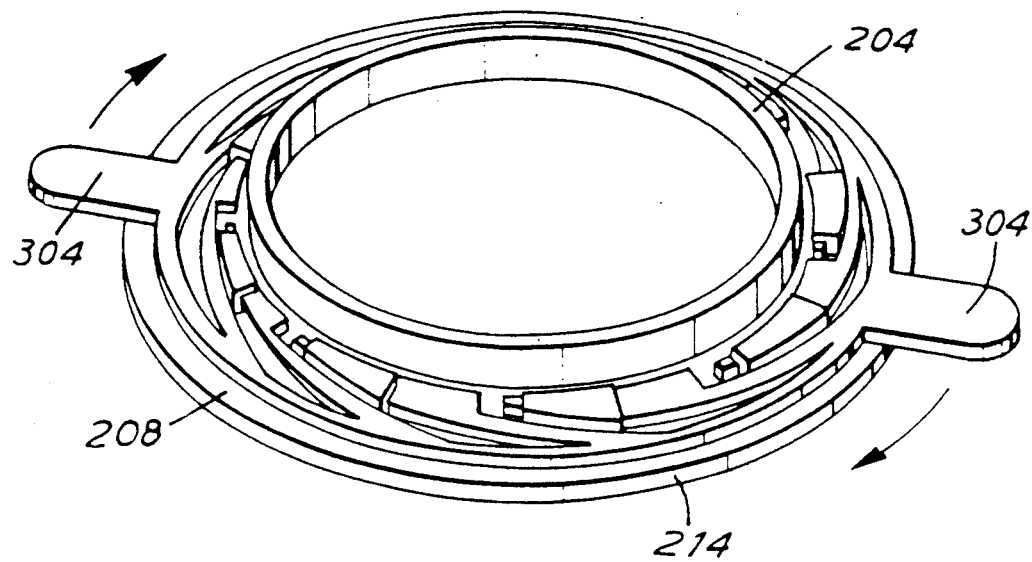
FIG. 4 is a perspective view showing the body-side coupling element and the locking member assembled, but omitting the bag-side coupling element for the sake of clarity.
Figure 7:
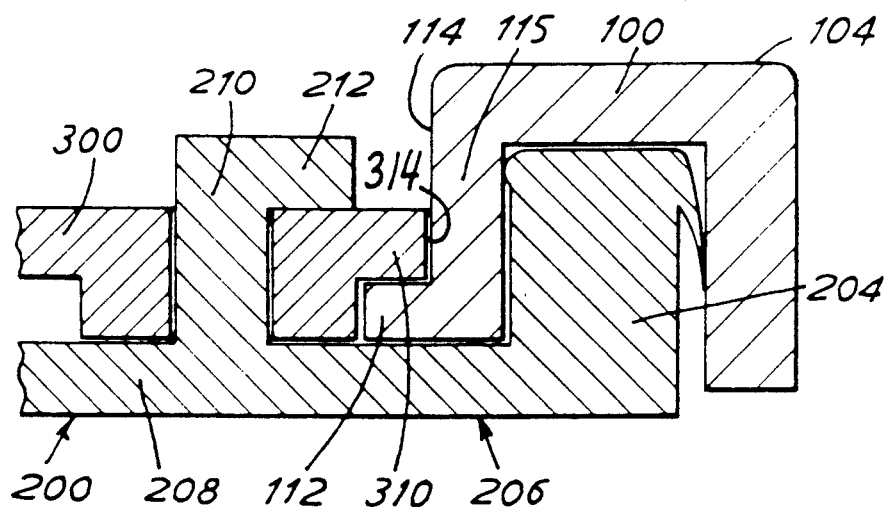
FIG. 7 is a radial plane through an assembled ostomy coupling including the bag side coupling element according to the invention taken along the lines and arrows 7—7 in FIG. 6.

As seen in FIG. 3, the lugs are disposed at a small angle to the tangential direction. When the locking member 300 is moved in a clockwise direction as seen in either FIG. 2 or FIG. 5, the angled configuration of the lugs causes the flexible arms 306 to be moved radially inward as the locking member rotates. When it moves in the opposite (anti-clockwise) direction, the inherent resilience of the plastics material causes the arms to spring back to the positions which they occupy as illustrated in FIG. 2. FIG. 6 shows the assembly (without the bag side coupling element 100 for clarity) in the lock position. Here the lugs 210 force the blade portions 310 radially inwardly to over-lie the flange 112 as shown in FIG. 7.

The coupling system specifically disclosed and illustrated herein has the advantage that a secure connection or interlocking can be achieved all the way round the stomal aperture. In some known three-part ostomy coupling systems, engagement has been provided only at opposite ends of a diameter or at opposite ends of two diameters at right angles. Clearly such arrangements are undesirably insecure, in that deformation of only two or four plastics interengaging elements can result in accidental separation of the coupling elements with potentially disastrous consequences. Another advantage of the coupling system disclosed herein is that the body-side coupling element and locking member can be employed with a bag-side coupling element which embodies all the proven successful features of an established product.

What is claimed is:

1. A coupling system for an ostomy bag including a bag-side coupling element having a stomal orifice surrounded by a channel shaped member, a body-side coupling element having a stomal orifice surrounded by a rib-like member which can make snap-fit engagement with the channel shaped member, and a locking member having radially inwardly deformable arms and which is rotatable relative to the body-side coupling, the deformable arms being shaped and positioned so that upon rotation of the locking member in one rotary direction relative to the body-side coupling element they are deformed radially inwardly and over-lie a portion of the bag-side coupling element.

2. A system according to claim 1 in which the locking member is generally annular and the arms are arcuate in shape each with a blade portion and a leg portion which connects the blade portion to the remainder of the locking member.

3. A system according to claim 1 in which a plurality of arms are spaced around and form the major part of the boundary of a central stomal aperture in the locking member.

4. A system according to claim 2 in which a plurality of arms are spaced around and form the major part of the boundary of a central stomal aperture in the locking member.

5. A system according to claim 3 in which the body-side coupling has upstanding lugs positioned to engage a part of the radially outer surface of each blade portion, these lugs being elongated in a circumferential direction and located so that they are at a small angle to the tangential direction.

6. A system according to claim 4 in which the body-side coupling has upstanding lugs positioned to engage a part of the radially outer surface of each blade portion, these lugs being elongated in a circumferential direction and located so that they are at a small angle to the tangential direction.

7. A system according to claim 5 in which the lugs have an inturned roof portion which over-lie the blade portions.

8. A system according to claim 6 in which the lugs have an inturned roof portion which over-lie the blade portions.

9. A system according to claim 4 in which the blade portions of the arms have their radially inner surfaces shaped so that in the locked position these inner surfaces together define a cylindrical surface of diameter substantially equal to the outer diameter of said channel member of the bag-side coupling element.

10. A system according to claim 5 in which the blade portions of the arms have their radially inner surfaces shaped so that in the locked position these inner surfaces together define a cylindrical surface of diameter substantially equal to the I.D. of the outer channel wall of the bag-side coupling element.

11. A system according to claim 6 in which the blade portions of the arms have their radially inner surfaces shaped so that in the locked position these inner surfaces together define a cylindrical surface of diameter substantially equal to the I.D. of the outer channel wall of the bag-side coupling element.

12. A system according to claim 7 in which the blade portions of the arms have their radially inner surfaces shaped so that in the locked position these inner surfaces together define a cylindrical surface of diameter substantially equal to the I.D. of the outer channel wall of the bag-side coupling element.

* * * * *